United States Patent [19]

Tamaoki et al.

[11] Patent Number: 5,206,153
[45] Date of Patent: Apr. 27, 1993

[54] METHOD OF PRODUCING HUMAN α-FETOPROTEIN AND PRODUCT PRODUCED THEREBY

[75] Inventors: Taiki Tamaoki, Alberta, Canada; Tomonori Morinaga, Tochigi; Shinzo Nishi, Hokkaido, both of Japan

[73] Assignee: Snow Brand Milk Products Co., Ltd., Hokkaido, Japan

[21] Appl. No.: 852,844

[22] Filed: Mar. 16, 1992

Related U.S. Application Data

[63] Continuation of Ser. No. 544,336, Jun. 27, 1990, abandoned.

[51] Int. Cl.$^5$ .................. C07K 13/00; C12N 15/62
[52] U.S. Cl. .................. 435/69.7; 435/252.3; 435/320.1; 530/350
[58] Field of Search .............. 530/350; 435/69.1, 69.7, 435/252.3, 320.1

[56] References Cited

U.S. PATENT DOCUMENTS 4,615,974 10/1986 Kingsman et al. ............... 435/172.3

OTHER PUBLICATIONS

J. Biochem. 104:968–972, Jun. 1988, Nishi et al. Expression of Rat α-Fetoprotein cDNA in *Escherichia coli* and in Yeast.
P.N.A.S. 80:4604–4608, Aug. 1983, Morinaga et al. Primary Structures of human α-fetoprotein and its mRNA.

*Primary Examiner*—Robert J. Hill, Jr.
*Assistant Examiner*—John D. Ulm
*Attorney, Agent, or Firm*—Burgess, Ryan & Wayne

[57] ABSTRACT

The present invention is directed to a method of producing recombinant human α-fetoprotein in which a DNA encoding a signal peptide for a rat α-fetoprotein is fused with a DNA encoding a human α-fetoprotein.

7 Claims, 2 Drawing Sheets

METHOD OF PRODUCING HUMAN α-FETOPROTEIN AND PRODUCT PRODUCED THEREBY

This application is a continuation of application Ser. No. 544,336, filed Jun. 27, 1990, now abandoned.

FIELD OF THE INVENTION

The present invention is generally directed to methods of producing recombinant human α-fetoprotein and particularly to a method of producing human α-fetoprotein in which a DNA sequence coding a signal peptide for rat α-fetoprotein is fused with DNA coding for human α-fetoprotein.

BACKGROUND OF THE INVENTION

α-fetoprotein is a major protein present in fetal serum. It is produced by the liver of fetal mammals as well as in the yolk sac. It is normally not present in children. Its appearance in the sera of children and adults is associated with hepatoma and yolk sac tumor, since these tumors specifically produce α-fetoprotein. The highly specific association of α-fetoprotein with such malignancies has attracted much interested.

The structure of α-fetoprotein, its genetic composition and the mechanism by which its genetic composition can be regulated has been extensively studied. DNA sequences complimentary to the mRNA sequence of α-fetoprotein have been cloned and the nucleotide sequences of the mRNAs and the amino acid sequences of the α-fetoprotein have been determined for the mouse (S>W>Law et al, Nature 291: 201-205) (1981); for the rat- L. L. Jagodzinski et al, Proc. Natl. Acad. Sci. 78: 3521-3525 (1981); and for humans-T. Morinaga et al Proc. Natl. Acad. Sci. 80: 4604-4608 (1983). The expression of rat α-fetoprotein cDNA in Escherichia coli and in yeast has also been reported in J. Biochem, 104, 968-972 (1988).

R. Boismenu et al, Life Sciences 43: 673-681 (1988) discloses the fusion of a mouse α-fetoprotein fragment of amino acid 256 to 548 with a portion of β-galactosidase in E. coli to provide a protein immunoreactive with anti-mouse α-fetoprotein anti-serum. T. Morinaga has also described human α-fetoprotein with a signal peptide of 19 amino acids and a mature human α-fetoprotein composed of 590 amino acids.

SUMMARY OF THE INVENTION

The present invention is directed to a recombinant protein which is immunoreactive in a manner closely resembling that of human α-fetoprotein and to a method of making the recombinant protein by inserting into an expression vector, the cDNA sequence coding for human mature α-fetoprotein fused with the signal peptide of rat α-fetoprotein. The resulting recombinant α-fetoprotein is purified and can be used in immunoassays for the detection of antihuman α-fetoprotein and thus for the diagnosis of hepatoma and yolk sac tumors.

In a preferred form of the invention, the chimera DNA comprised of the fused cDNA sequence for human α-fetoprotein and the rat-α-fetoprotein signal peptide is inserted into a plasmid containing a DNA fragment of yeast, preferably from Saccharomyces cerevisiae containing an acid phosphatase promotor, an autonomous replication origin, the leu 2 gene, and a second DNA fragment containing an ampilicilline-resistant gene. The resulting cells harboring the plasmids are cultured and the recombinant α-fetoprotein is isolated and purified. The immunological properties of the resulting recombinant human α-fetoprotein is similar to that of natural human α-fetoprotein.

BRIEF DESCRIPTION OF THE DRAWINGS

The following drawings are illustrative of embodiments of the invention and are not intended to limit the invention as encompassed by the claims forming part of the application.

In one aspect, the invention is directed to a method for producing α-fetoprotein and comprises the steps of:

(a) fusing a DNA sequence coding a signal peptide for rat α-fetoprotein into the 5' terminal site of cDNA for mature human α-fetoprotein to form a chimera DNA;

(b) inserting the chimera DNA into a vector;

(c) inserting the vector into a yeast cell to thereby form cells capable of expressing human-α-fetoprotein;

(d) culturing the yeast cells obtained from step (c) in a culture medium; and (e) isolating human α-fetoprotein from the cultured medium. In the method the chimera DNA can be inserted into a plasmid containing a DNA fragment of yeast and acid phosphotase promoter, an autonomous replication origin DNA, the Leu 2 gene and a second DNA fragment containing a replication origin and an ampilicilline-resistant gene. As the plasmid containing the DNA fragment of yeast one can use pAM82. The DNA fragment is obtained from E-coli plasmid pBR322.

The method of the invention can be further defined as comprising the step of:

(i) digesting plasmid pAMRA1 with ScaI;

(ii) ligating the BamH1 linkers formed in step (i);

(iii) isolating a fragment containing the DNA sequence for coding the signal peptide for rat α-fetoprotein;

(iv) ligating the fragment obtained in step (iii) with human α-fetoprotein in said plasmid pAMARA1; and (v) inserting the ligated product of step (iv) into the XhoI site of the vector pAM82.

The rat AFP signal peptide sequence is as follows:

[CCTCGAGG] GGG ATG AAG CAG CCA GCA ACC ATG AAG TGG AGC, GCA
Xho I Linker  Met Lys Gln Pro Ala Thr Met Lys  Trp Ser Ala TCC ATT TCC TTC CTT CTC CTG CTA AAT TTT GCT GAA CCC AGA GTCCC[GGATCC]
Ser Ile Ser phe Leu Leu Leu Leu Asn phe Ala Glu Pro Arg       BamHI
                                                               Linker

DETAILED DESCRIPTION OF THE INVENTION

Figure 1:
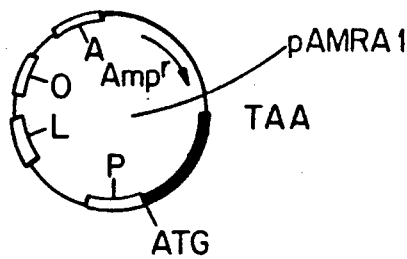
FIG. 1 depicts the structure of pAMRA1 which contains the cDNA sequence encoding the entire rat α-fetoprotein polypeptide.

Plasmid pAMRA1 having the structure shown in FIG. 1 was constructed inserting the SaII/XhoI fragment which was prepared from the plasmid pKRA1 and contains entire coding sequence for rat α-fetoprotein into the XhoI site of the pAM82 vector. The detailed procedure for the construction of pAMRA1 is as follows.

First, pBRA1, a plasmid containing the cDNA for rat α-fetoprotein was partially digested with PstI. The two killo base (kb) fragment that contained the cDNA was isolated by agarose gel electrophoresis. The fragment was digested with Bal 31 to remove the nucleotide upstream of the initiation codon and then digested with HincII. The 1.9 kb fragment thus generated was isolated by an agarose gel electrophoresis and inserted at the SmaI site of pKK223-3. The plasmid produced was termed pKRA1.

Plasmid pKRA1 was linearized by SmaI digestion and XhoI linkers were ligated at the ends. After digesting this product with XhoI and SaII. the 1.9 kb fragment containing the α-fetoprotein cDNA was isolated by electrophoresis and inserted into the XhoI site of pAM82. This product was named pAMRA1.

Figure 2:
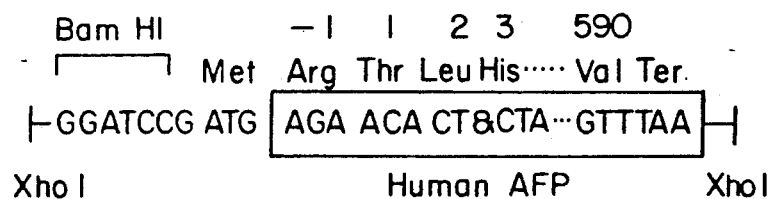
FIG. 2 depicts the structure of pAMHA1 coding for human α-fetoprotein.
Figure 3:
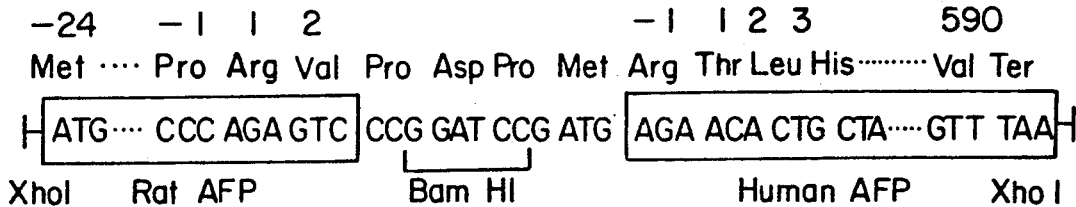
FIG. 3 is a schematic view of the structure of the expression plasmid p-AMHA3 designed to express a human α-fetoprotein of 590 amino acid residues having two extra amino acids at the N-terminus and to encode 26 amino acids present at the N-terminus of rat pre α-fetoprotein and three amino acids derived from a linker.

Plasmid pAMRA1 was digested with ScaI and the BamHI linkers were ligated at the ends. Fragments generated by the digestion of the DNA with BamHI and XhoI was separated by gel electrophoresis and the desired DNA fragment that encode the signal peptide portion of the rat α-fetoprotein was extracted from the gel. The DNA fragment thus obtained was ligated to the human α-fetoprotein cDNA in pAMHA1 having the structure shown in FIG. 3. The fused chimera was then inserted into the XhoI site of the expression vector pAM82 as shown in FIG. 3. The fused α-fetoprotein DNA sequence encodes 24 amino acids of rat α-fetoprotein signal peptide and three extra amino acids derived from the linker in addition to the amino acid residues encoded by that of pAMHA1 shown in FIG. 2.

EXAMPLE

For this example the procedure set forth in *Proc. Natl. Acad. Sci. USA* Vol. 75, No. 4, pp 1929-1933, April 1978, was followed.

The expression plasmid pAMHA3 was propagated in *E coli* HB101 and introduced to yeast AH22 (a leu 2 his can cir+) by the method described by Hinnen et al as follows. Leu+ transformants were selected on 2% agar plates prepared in Burkholder minimal medium fortified with histidine (20 mg/liter) and 1.5 grams of $KH_2PO_4$ per liter (high-Pi medium). The content of the Burkholder Medium (per liter) as disclosed in *Am. J. Bot.*, 30, 206 (1943) is as follows:

| | |
|---|---|
| $(NH_4)_2SO_4$ | 2 g |
| Biotin | 2 μg |
| Pantothenic acid-Ca | 200 μg |
| Inositol | 10,000 μg |

-continued

| | |
|---|---|
| Pyridoxine HCl | 200 μg |
| Thiamine HCl | 200 μg |
| $H_3BO_3$ | 30 μg |
| $CuSO_4.5H_2O$ | 20 μg |
| KI | 400 μg |
| $FeCl_3\ 6H_2O$ | 125 μg |
| $MnSO_4.7H_2O$ | 50 μg |
| $Na_2Mo)_4.2H_2O$ | 100 μg |
| $ZnSO_4.7H_2O$ | 150 μg |
| $KH_2PO_4$ | 1.5 g (for high-P med only) |
| KCl | 1.5 g (for low-P med only) |
| $MgSO_4H2O$ | 0.5 g |
| $CaCl_22H_2O$ | 0.33 g |

AH22 cells harboring the expression plasmids were grown in Burkholder minimal medium containing 1.5 g/liter of KCl (low-Pi medium) at 30° C. with aeration to a cell density of $2 \times 10^7$ cells per ml. The cells were collected by centrifugation at 3.000 rpm for 20 min. and cultured in the low-Pi medium.

When the density reached $1 \times 10^8$ cells per ml, the induced cells were collected by centrifugation. A cell lysate was prepared from the spheroplasts of the induced yeast cells. The cells were collected and suspended in 100 μg/ml of Zymolyase-100T (Seikagaku Kogyo)/1M sorbitol/50 mM phosphate (pH 7.2)/50 mM EDTA (pH 7.2)/14 mM mercaptoethanol and incubated at 30° C. for 2 hours under gentle shaking. The resultant spheroplasts were collected by centrifugation, lysed with 20 mM Tris-HCl (pH 7.5)/0/5M NaCl/0.1% Triton X-100/0.1 mM phenylmethylsulfonyl fluoride at 0° C. for 1 hr and centrifuged at 8,000 rpm for 15 minutes.

Figure 4:
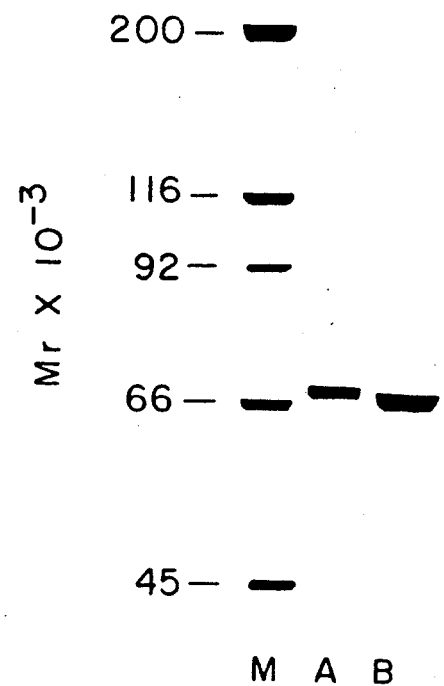
FIG. 4 is an SDS-polyacrylamide gel electrophoresis analysis showing natural purified human α-fetoprotein, the recombinant α-fetoprotein of the present invention and standard molecular size markers.

The supernatant thus prepared was used for the analysis and purification of the recombinant α-fetoprotein. The recombinant α-fetoprotein was isolated to a high degree of purity from the lysate of yeast cells harboring pAMHA3. 19.8 grams of yeast cells were obtained from 4 liters of culture and 180 ml of the lysate prepared from them contained 251 μg of the α-fetoprotein. The eluate from the DEAE-cellulose column was found to contain 214 μg of α-fetoprotein in a volume of 180 ml and 118 μg of α-fetoprotein was recovered in a purified form from the immunoadsorbent column. The purified α-fetoprotein was concentrated and the buffer was replaced with distilled water by the use of Centricon 30 (Amicon). The amounts of the total protein in the lysate and the eluate from the DEAE-cellulose column were 239 mg and 29.7 mg, respectively. Upon analysis by SDS1-polyacrylamide gel electrophoresis, the purified recombinant α-fetoprotein migrated as a single but somewhat dispersed band and no impurity was detected as shown best in FIG. 4. Molecular weights calculated for the recombinant and natural α-fetoprotein were 68,000 and 69,000 respectively.

Natural human-α-fetoprotein has one glycosilation site. The observed minor difference of the molecular sizes of the natural and recombinant α-fetoprotein is believed to be due to the carbohydrate moieties since yeast cells are known to glycosylate differently from mammalian cells. The recombinant α-fetoprotein was shown by automated Edman degradation analysis to have the following N-terminal sequence.

Xaa-Val-Pro-Asp-Pro-Met-Xaa-Thr-Leu-His (Xaa: unidentified residue)

The sequence indicated that the yeast cells produced pre α-fetoprotein and cleaved off the signal peptide at the same position as in rat cells. In spite of the entry into endoplasmic reticulum and thus into the secretory pathway as evidenced by the processing of the signal peptide, α-fetoprotein was not secreted into the medium. A small amount of α-fetoprotein detected in the supernatant obtained at centrifugation to prepare spheroplasts perhaps indicate the presence of α-fetoprotein of the periplasmic cavity.

Figure 5:
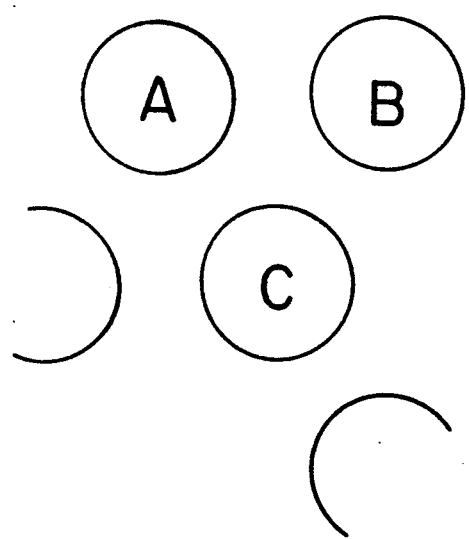
FIG. 5 depicts the immunoassay activity of the recombinant α-fetoprotein of the present invention to affinity-purified horse antibody to human α-fetoprotein as compared with natural purified α-fetoprotein.

In a Ouchterlony double immunodiffusion test, natural and recombinant fetoprotein formed a completely fused precipitating line with horse antibody to human α-fetoprotein as shown in FIG. 5. The recombinant and authentic α-fetoprotein reacted equally in radioimmunoassay systems using radioiodinated polyclonal antibody to α-fetoprotein and one of the solid phase antibodies of AFY1-AFY6. Amino acid analysis of the recombinant α-fetoprotein indicated that it had an amino acid composition similar to that expected for the amino acid sequence of human α-fetoprotein and the additional N-terminal residues shown in Table 1.

TABLE 1

| Amino Acid Composition of Recombinant AFP | | |
|---|---|---|
| Residues | Found | Predicted |
| Asp+Asn | 45.3 | 43(24 + 19) |
| Thr | 34.2 | 35 |
| Ser | 35.2 | 36 |
| Glu—Gln | 97.3 | 97(57 + 40) |
| Pro | 24.3 | 23 |
| Gly | 35.2 | 25 |
| Ala | 48.9 | 51 |

TABLE 1-continued

| Amino Acid Composition of Recombinant AFP | | |
|---|---|---|
| Residues | Found | Predicted |
| 1/2Cys | N.2. | 32 |
| Val | 29.7 | 30 |
| Met | 7.4 | 9 |
| Ile | 28.8 | 32 |
| Leu | 55.6 | 57 |
| Tyr | 15.8 | 17 |
| Phe | 28.4 | 29 |
| Lys | 41.1 | 41 |
| His | 15.2 | 16 |
| Arg | 21.9 | 23 |
| Trp | N.D. | 1 |
| TOTAL | (564.0) | (597) |

[a]Values are residues/AFP molecule. [b]Values are those of AFP produced and processed by yeast cells. [c]Cys and Trp were not determined.

Further discussion of the method of the present invention is set forth in a paper entitled "Discussion of Human α-fetoprotein-in yeast" which was presented at the 26th Regular meeting of the Hokkaido Branch of the Japanese Biochemical Society on Jul. 1, 1989, the subject matter of such paper being hereby incorporated herein by reference.

We claim:

1. A modified recombinant α-fetoprotein comprised of an amino acid sequence of Arg-Val-Pro-Asp-Pro-Met-Arg-Thr-Leu-His, which is a signal peptide of a rat α-fetoprotein and a peptide linker, and an amino acid sequence of mature human α-fetoprotein in which said signal peptide and peptide linker are fused at the 5' terminal site of said mature human α-fetoprotein.

2. A recombinant DNA encoding the modified recombinant α-fetoprotein of claim 1.

3. A vector comprising the DNA of claim 2.

4. A vector according to claim 3 which is the plasmid p-AMHA3.

5. A host cell comprising the vector of claim 3.

6. A yeast cell comprising the vector of claim 4.

7. A method for producing α-fetoprotein comprising culturing the yeast cells of claim 6 and isolating human α-fetoprotein from the culture medium.

* * * * *

UNITED STATES PATENT AND TRADEMARK OFFICE
CERTIFICATE OF CORRECTION

PATENT NO. : 5,206,153
DATED : April 27, 1993
INVENTOR(S) : Taiki Tamaoki, et al It is certified that error appears in the above-indentified patent and that said Letters Patent is hereby corrected as shown below:

TITLE PAGE

In the Abstract:

line 3: "a signal peptide for a" should read --the signal peptide for--.

line 4: "a human" should read --the human--.

In the Drawings:

Fig. 5 should read:

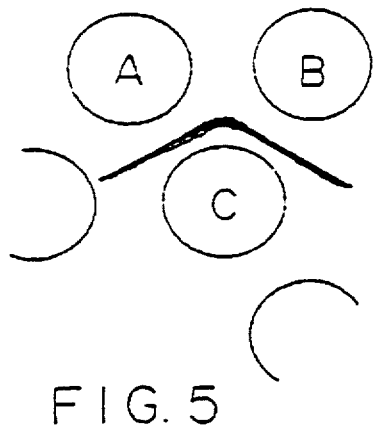

FIG. 5

UNITED STATES PATENT AND TRADEMARK OFFICE
CERTIFICATE OF CORRECTION

PATENT NO. : 5,206,153
DATED : April 27, 1993
INVENTOR(S) : Taiki Tamaoki, et al It is certified that error appears in the above-indentified patent and that said Letters Patent is hereby corrected as shown below:

Column 1, line 26: "interested." should read --interest.--.

line 34: "S>W>" should read --S.W.--.

Column 2, line 21: "p-AMHA3" should read --pAMHA3--.

line 28: "natural purified" should read --purified natural--.

line 28: " α-fetoprotein" should read --α-fetoprotein (A)--.

line 29: "invention" should read --invention (B)-- line 30: "markers" should read --markers (M)--.

line 34: "natural purified" should read --purified natural--.

UNITED STATES PATENT AND TRADEMARK OFFICE
CERTIFICATE OF CORRECTION

PATENT NO. : 5,206,153
DATED : April 27, 1993
INVENTOR(S) : Taiki Tamaoki, et al It is certified that error appears in the above-indentified patent and that said Letters Patent is hereby corrected as shown below:

Column 2, line 38: "sequence coding" should read --encoding-- line 39: "α-fetoprotein into" should read --α-fetoprotein--.

line 53: "the plasmid" should read --plasmid--.

line 54: "yeast one" should read --yeast, one--.

line 60: "linkers" should read --linkers to the DNA--.

line 62: "for coding" should read --coding--.

line 65: "pAMARA1" should read --pAMHA1--.

Column 3, line 3: that portion of the sequence reading "GTCCC[GGATCC] BamHI Linker" should read GTCCC[GGATCC] BamHI Linker--.

line 13: "SalI" should read --Sall--.

line 43: "Fig. 3" should read --Fig. 2--.

line 45: "The fused α-fetoprotein" should read --The fused--.

UNITED STATES PATENT AND TRADEMARK OFFICE
CERTIFICATE OF CORRECTION

PATENT NO. : 5,206,153
DATED : April 27, 1993
INVENTOR(S) : Taiki Tamaoki, et al It is certified that error appears in the above-indentified patent and that said Letters Patent is hereby corrected as shown below:

Column 3, line 46: "DNA sequence" should read --DNA--.

line 49: "by that of" should read --the cDNA for human -fetoprotein in--.

last line: "Inositol      10,000 ug" should read: --Inositol     10,000ug
         Nicotinic acid    200ug--.

Column 4, line 16: "Na$_2$Mo)$_4$.2H$_2$O" should read --Na$_2$Mo$_4$.H$_2$O--.

line 19: "MgSO$_4$H20" should read --MgSO$_4$.7H$_2$O--.

line 57: "SDS1-" should read --SDS- --.

Column 5, line 35: "Found" and "Predicted" should read --Found$^a$-- and --Predicted$^b$--.

line 40: "Glu - Gln" should read --Glu + Gln--.

Column 6, line 5: "N.2." should read --N.D.$^c$--.

line 13: "N.D." should read --N.D.$^c$--.

UNITED STATES PATENT AND TRADEMARK OFFICE
CERTIFICATE OF CORRECTION

PATENT NO. : 5,206,153

DATED : April 27, 1993

INVENTOR(S) : Taiki Tamaoki, et al

It is certified that error appears in the above-indentified patent and that said Letters Patent is hereby corrected as shown below:

Column 6, line 19: "Discussion" should read --Expression--.

line 21: "Regular" should read --Annual--.

last line: "culture medium." should read --yeast cells.--.

Signed and Sealed this

Fourth Day of October, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,206,153
DATED     : April 27, 1993
INVENTOR(S) : Taiki Tamaoki, et al.

It is certified that error appears in the above-identified patent and that said Letters Patent is hereby corrected as shown below:

Column 2, line 39; "α-fetoprotein" should read -- α-fetoprotein to --.
          lines 54-55; delete "the DNA fragment is obtained from E-coli plasmid pBR322."
          line 62; "coding" should read -- coding for --.
Column 3, line 13; "SaII" should read -- SalI --.
          line 49; "the cDNA for human -fetoprotein in" should read -- by the cDNA for human -α-fetoprotein in --.
Column 4, line 16; "Na$_2$Mo$_4$·H$_2$O" should read -- Na$_2$MO$_4$.2H$_2$O --.
Column 5, lines 29-31; "for the amino acid sequence of human α-fetoprotein and the additional N-terminal residues shown in Table 1." should read -- from the nucleotide sequence of the DNA that had been cloned in pAMHA3. --.

Signed and Sealed this

Twenty-second Day of August, 1995

Attest:

BRUCE LEHMAN

Attesting Officer     Commissioner of Patents and Trademarks